United States Patent
Tamura et al.

(10) Patent No.: US 7,109,286 B2
(45) Date of Patent: Sep. 19, 2006

(54) PHOSPHORUS-CONTAINING HYDROQUINONE DERIVATIVES, PROCESS FOR THEIR PRODUCTION, PHOSPHORUS-CONTAINING EPOXY RESINS MADE BY USING THE DERIVATIVES, FLAME-RETARDANT RESIN COMPOSITIONS, SEALING MEDIA AND LAMINATED SHEETS

(75) Inventors: Ken Tamura, Tokyo (JP); Eiichi Tatsuya, Tokyo (JP); Yoshirou Kaneda, Tokyo (JP); Natsuhiro Sano, Tokyo (JP)

(73) Assignee: Nippon Chemical Industrial Co., Ltd., Koto-ku (JP)

( * ) Notice: Subject to any disclaimer, the term of this patent is extended or adjusted under 35 U.S.C. 154(b) by 0 days.

(21) Appl. No.: 10/312,403

(22) PCT Filed: Jun. 20, 2001

(86) PCT No.: PCT/JP01/05271

§ 371 (c)(1),
(2), (4) Date: Dec. 26, 2002

(87) PCT Pub. No.: WO02/00667

PCT Pub. Date: Jan. 3, 2002

(65) Prior Publication Data

US 2003/0125433 A1    Jul. 3, 2003

(30) Foreign Application Priority Data

Jun. 29, 2000  (JP) .............................. 2000-195769
Jun. 29, 2000  (JP) .............................. 2000-195770

(51) Int. Cl.
C08G 59/04    (2006.01)
C08G 59/02    (2006.01)
C07F 9/6568   (2006.01)
C07F 9/02     (2006.01)

(52) U.S. Cl. ........................... 528/99; 568/15; 568/17; 525/523

(58) Field of Classification Search ............... 528/99; 568/15, 17; 525/523
See application file for complete search history.

(56) References Cited

U.S. PATENT DOCUMENTS 6,291,626 B1 *  9/2001  Wang et al. .................. 528/99

FOREIGN PATENT DOCUMENTS

| JP | 64-51431 A | | 2/1989 |
| JP | 64-66195 A | | 3/1989 |
| JP | 4-8758 | * | 1/1992 |
| JP | 11-166035 | * | 6/1999 |
| JP | 11-279258 | * | 10/1999 |
| JP | 2000-143942 A | | 5/2000 |
| JP | 2002-265562 | * | 9/2002 |

OTHER PUBLICATIONS

Derwent Abstract of JP'562.*
Chem. Abstracts abstract of JP'562.*
Abstract JP 4-8758 Jan. 13, 1992.*
Abstract JP 11-166035 Jun. 22, 1999.*
Abstract JP 11-279258 Oct. 12, 1999.*

* cited by examiner

*Primary Examiner*—Margaret G. Moore
(74) *Attorney, Agent, or Firm*—Smith Patent Office

(57) ABSTRACT

A phosphorus-containing hydroquinone derivative represented by a general formula (1):

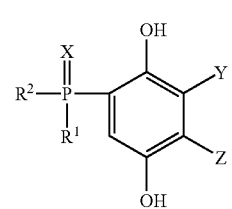

(where $R^1$ and $R^2$ represent linear or branched alkyl groups that are identical or may be different, and/or $R^1$ and $R^2$ may form a circular group; X represents an oxygen atom or sulfur atom; Y and Z represent hydrogen atom, hydroxy group, linear or branched alkyl group, aralkyl group, alkoxy group, allyl group, aryl group or cyano group, and/or Y and Z may form a circular group). The present invention provides phosphorus-containing hydroquinone derivatives that are useful for intermediate materials for reactive type flame-retardant agents or phosphorus-containing epoxy resins.

26 Claims, No Drawings

PHOSPHORUS-CONTAINING HYDROQUINONE DERIVATIVES, PROCESS FOR THEIR PRODUCTION, PHOSPHORUS-CONTAINING EPOXY RESINS MADE BY USING THE DERIVATIVES, FLAME-RETARDANT RESIN COMPOSITIONS, SEALING MEDIA AND LAMINATED SHEETS

TECHNICAL FIELD

The present invention relates to phosphorus-containing hydroquinone derivatives useful for reactive type flame-retardant agents that are used for adding flame-retardancy to epoxy resins and so on, process for production thereof, phosphorus-containing epoxy resins using thereof, flame-retardant epoxy resin compositions, sealant and laminates.

BACKGROUND ART

Epoxy resins are employed for a wide range of applications such as electronic components, electrical equipment, automotive parts, FRP, sporting equipment and so on, since the epoxy resins have better adhesiveness, better heat resistance and better moldability. Among them, flame-retardant agents, in particular brominated epoxy resins or antimony compounds are employed for copper-clad laminates and sealant that are employed for electronic components and electrical equipment. However, halogen-containing compounds or antimony compounds cause concerns about human safety, and therefore flame-retardant agents that have taken the environment into consideration are desired.

Conventionally, as the methods for adding flame-retardancy to epoxy resins, methods of kneading an additive-type flame-retardant agent to an epoxy resin, of modifying the epoxy resins by using a reactive flame-retardant agent whereby chemically reacting an epoxy resin and a flame-retardant agent, and so on, have been proposed.

Proposed methods of using an additive-type flame-retardant agent includes, for example: a method using alumina hydrate (Japanese Patent Application Laid-open No. H05-25369); a method of using modified red phosphorus (Japanese Patent Application Laid-open No. S63-156860); a method of using modified red phosphorus, alumina hydrate and silica powder (Japanese Patent Application Laid-open No. S58-198521) and so on.

However, using these additive-type flame-retardant agents may require larger amounts of the flame-retardant agents, thereby causing a problem of deterioration of the moldability of the compound material.

On the contrary, various methods of using reactive flame-retardant agents have been proposed since smaller amounts of flame-retardant agents are necessary.

For example, proposed methods includes: a method of using tris(hydroxypropyl)phosphine oxide (Japanese Patent Application Laid-open No. S57-195141), a method using phosphine oxide derivatives as represented by the following general formula (4):

(where x=0 to 2; y=1 to 3; and x+y=3; R represents methylene group or ethylene group) (Japanese Patent Application Laid-open No. S63-95223); a method of using organophosphorus compound as represented by the following general formula (5):

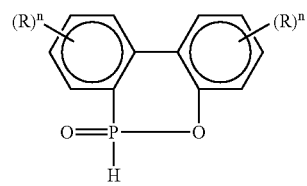

or the following general formula (6):

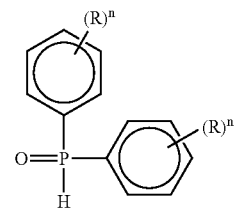

(where R is alkyl group-containing 1 to 6 carbons and n represents a number from 0 to 4) (Japanese Patent Application Laid-open No. H11-279258 and H11-166035); a method of using polyepoxy phosphonate compounds that is obtainable by reacting phosphonic acid with polyepoxy compounds having oxysilane group or epihalohydrin (Japanese Patent Application Laid-open No. S51-143620, H03-84025, H02-272014 and H02-269730) and so on.

Also, Japanese Patent Application Laid-open No. 2000-80251 discloses a method of using phosphorus-containing compounds having a general formula (7) of:

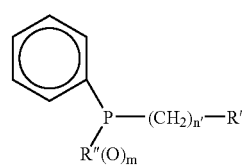

(where R' is a compound including two or more phenolic OH; n is an integer number of 0 to 3; R" is a linear or branched alkyl group having 1 to 8 carbons, cyclohexyl group, cyclopentyl group or aryl group, or alkyl-substituted or alkoxy-substituted alkyl group or aryl group having 1 to 18 carbons; wherein R" may create a cyclic form with P atom; and m is 0 or 1).

Although various methods for adding flame-retardancy to epoxy resins with reactive flame-retardant agents have been proposed as described above, there are problems such as the difficulty in increasing phosphorus content in epoxy resins to a level where the flame-retardant effect is revealed or the difficulty in increasing flame-retardancy, or problems in which materials having phosphorus-oxygen bonds are inferior in moisture resistance and chemical resistance.

That is, an object of the present invention is to provide novel phosphorus-containing hydroquinone derivatives useful for reactive flame-retardant agents having phenolic hydroxyl group that reacts epoxy resins or epichlorohydrin and methods of producing them, and to provide phosphorus-containing epoxy resins produced by using the resultant phosphorus-containing hydroquinone derivatives, and further to provide flame-retardant epoxy resin compounds, sealant and laminates including phosphorus-containing epoxy resins and having improved flame-retardancy and chemical resistance.

DISCLOSURE OF INVENTION

The present inventors have found that the object described above can be achieved by using a phosphorus-containing hydroquinone derivative and by introducing into an epoxy resin a structural unit derived from the phosphorus-containing hydroquinone derivatives represented by the following general formula (1), to thus complete the present invention.

That is, a first aspect of the present invention is achieved by providing a phosphorus-containing hydroquinone derivative, which is characterized by the following general formula (1):

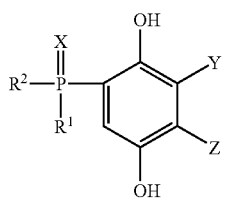

(1)

(where $R^1$ and $R^2$ represent linear or branched alkyl groups that may be identical or different, and/or $R^1$ and $R^2$ may form a circular group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group).

Further, a second aspect of the present invention is a method for producing the phosphorus-containing hydroquinone derivatives represented by the aforementioned general formula (1).

The method for producing a phosphorus-containing hydroquinone derivative represented by the aforementioned general formula (1) is characterized by reacting at least one compound selected from secondary phosphine derivatives represented by the following general formula (2):

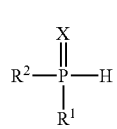

(2)

(where $R^1$, $R^2$ and X are the same as shown above); with a benzoquinone derivative represented by the following general formula (3):

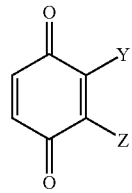

(3)

(where X and Z are the same as shown above).

Further, a second method for producing the phosphorus-containing hydroquinone derivatives represented by the aforementioned general formula (1) is achieved by a method characterized by reacting at least one compound selected from secondary phosphine derivatives represented by the following general formulas (2) and (2a):

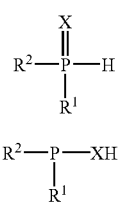

(2)

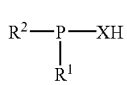

(2a)

(where $R^1$, $R^2$ and X are the same as represented above); with the benzoquinone derivative represented by the following general formula (3):

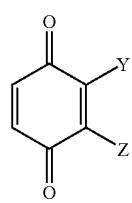

(3)

(where X and Z are the same as shown above).

Further, a third aspect of the present invention is a phosphorus-containing epoxy resin characterized in containing a structural unit derived from a phosphorus-containing hydroquinone derivative represented by the aforementioned general formula (1).

The phosphorus-containing epoxy resin may preferably be a compound obtainable by reacting the phosphorus-containing hydroquinone derivative represented by the aforementioned general formula (1) with an epihalohydrin, or compound obtainable by reacting the phosphorus-containing hydroquinone derivative represented by the aforementioned general formula (1) with a polyepoxy compound.

A fourth aspect of the present invention is a flame-retardant epoxy resin composition characterized in containing the aforementioned phosphorus-containing epoxy resin and a curing agent or a polymerization initiator.

A fifth aspect of the present invention is a sealant that is formed by using the aforementioned flame-retardant epoxy resin composition. The sealant may preferably be a flame-retardant sealant adopted for circuit boards for electric parts.

A sixth aspect of the present invention is laminates that are formed by using the aforementioned flame-retardant epoxy resin composition. The laminates may preferably be flame-retardant laminates adopted for electric parts.

BEST MODE FOR CARRYING OUT THE INVENTION

The present invention will be described in detail as follows.

The phosphorus-containing hydroquinone derivatives according to the present invention are represented by the following general formula (1):

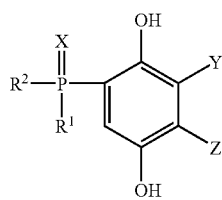

(1)

where $R^1$ and $R^2$ represent linear or branched alkyl group, wherein the alkyl group has 1–18 carbon atoms, preferably 1–8 carbons, and more specifically, the $R^1$ and $R^2$ may be exemplified by alkyl groups such as: methyl; ethyl; propyl; isopropyl; tertiary butyl; cyclobutyl; cyclopentyl; cyclohexyl and so on. $R^1$ and $R^2$ may be identical or different, and $R^1$ and $R^2$ may combine together at a point other than that of the phosphorus atom to form a circular group.

Examples of $R^1$ and $R^2$ forming a circular group can be represented as: propylene group; butylene group; pentamethylene group; hexamethylene group; heptamethylene group; cyclopentylene group; cyclohexylene group; cycloheptylene group; cyclooctylene group; cyclononylene group and so on.

X represents an oxygen atom or sulfur atom, preferably an oxygen atom.

Y and Z may represent: a hydrogen atom; hydroxy group; linear or branched alkyl group; aralkyl group such as benzyl and the like; allyl group; aryl group such as phenyl and the like, alkoxy group such as methoxy, ethoxy, propoxy, phenyloxy and the like; or cyano group. The alkyl group may have 1–18 carbon atoms, preferably 1–6 carbon atoms, and is more specifically exemplified by alkyl groups such as: methyl; ethyl; propyl; isopropyl; tertiary butyl; cyclohexyl and so on. Also, Y and Z may be identical or different, and Y and Z may form a circular group.

The examples of Y and Z forming a circular group can be represented as: propylene; butylene; pentamethylene; hexamethylene; heptamethylene; cyclohexylene; phenylene; biphenylene; benzoic and so on. Further, these groups may contain a hetero atom such as an oxygen atom, sulfur atom and nitrogen atom and so on.

The specific compounds of the phosphorus-containing hydroquinone derivatives includes an oxygen atom or sulfur atom attached to the following compounds represented by the general formula (1) and are exemplified as:
dimethyl phosphonyl-1,4-hydroquinone;
diethyl phosphonyl-1,4-hydroquinone;
di-n-propyl phosphonyl-1,4-hydroquinone;
di-iso-propyl phosphonyl-1,4-hydroquinone;
di-n-butyl phosphonyl-1,4-hydroquinone;
di-sec-butyl phosphonyl-1,4-hydroquinone;
di-tert-butyl phosphonyl-1,4-hydroquinone;
methylethyl phosphonyl-1,4-hydroquinone;
methyl-n-propyl phosphonyl-1,4-hydroquinone;
methyl-n-butyl phosphonyl-1,4-hydroquinone;
methyl-iso-butyl phosphonyl-1,4-hydroquinone;
methyl-sec-butyl phosphonyl-1,4-hydroquinone;
methyl-tert-butyl phosphonyl-1,4-hydroquinone;
ethyl-n-propyl phosphonyl-1,4-hydroquinone;
ethyl-iso-propyl phosphonyl-1,4-hydroquinone;
ethyl-tert-butyl phosphonyl-1,4-hydroquinone;
n-propyl-iso-propyl phosphonyl-1,4-hydroquinone;
n-propyl-n-butyl phosphonyl-1,4-hydroquinone;
n-butyl-sec-butyl phosphonyl-1,4-hydroquinone;
n-butyl-tert-butyl phosphonyl-1,4-hydroquinone;
propylene phosphonyl-1,4-hydroquinone;
butylene phosphonyl-1,4-hydroquinone;
pentamethylene phosphonyl-1,4-hydroquinone;
hexamethylene phosphonyl-1,4-hydroquinone;
1,4-cyclopentylene phosphonyl-1,4-hydroquinone;
1,4-cyclooctylene phosphonyl-1,4-hydroquinone;
1,5-cyclooctylene phosphonyl-1,4-hydroquinone;
diethyl phosphonyl-1,4-naphthalenediol;
dimethyl phosphonyl-1,4-naphthalenediol;
di-n-propyl phosphonyl-1,4-naphthalenediol;
di-iso-propyl phosphonyl-1,4-naphthalenediol;
di-n-butyl phosphonyl-1,4-naphthalenediol;
di-sec-butyl phosphonyl-1,4-naphthalenediol;
di-tert-butyl phosphonyl-1,4-naphthalenediol;
methylethyl phosphonyl-1,4-naphthalenediol;
methyl-n-propyl phosphonyl-1,4-naphthalenediol;
methyl-n-butyl phosphonyl-1,4-naphthalenediol;
methyl-iso-butyl phosphonyl-1,4-naphthalenediol;
methyl-sec-butyl phosphonyl-1,4-naphthalenediol;
methyl-tert-butyl phosphonyl-1,4-naphthalenediol;
ethyl-n-propyl phosphonyl-1,4-naphthalenediol;
ethyl-iso-propyl phosphonyl-1,4-naphthalenediol;
ethyl-tert-butyl phosphonyl-1,4-naphthalenediol;
n-propyl-iso-propyl phosphonyl-1,4-naphthalenediol;
n-propyl-n-butyl phosphonyl-1,4-naphthalenediol;
n-propyl-sec-butyl phosphonyl-1,4-naphthalenediol;
n-propyl-tert-butyl phosphonyl-1,4-naphthalenediol;
propylene phosphonyl-1,4-naphthalenediol;
butylene phosphonyl-1,4-naphthalenediol;
pentamethylene phosphonyl-1,4-naphthalenediol;
hexamethylene phosphonyl-1,4-naphthalenediol;
1,4-cyclopentylene phosphonyl-1,4-naphthalenediol;
1,4-cyclooctylene phosphonyl-1,4-naphthalenediol;
1,5-cyclooctylene phosphonyl-1,4-naphthalenediol; and so on.

Here, the aforementioned phosphorus-containing hydroquinone derivatives according to the present invention may be a mixture of the phosphorus-containing hydroquinone derivatives derived from the reactant materials.

Next, the method for producing the phosphorus-containing hydroquinone derivatives according to the present invention will be described.

The phosphorus-containing hydroquinone derivatives represented by the aforementioned general formula (1) according to the present invention are characterized in being obtained by reacting at least one compound selected from secondary phosphine derivatives represented by the following general formula (2) with a benzoquinone derivative represented by the following general formula (3).

In the secondary phosphine derivatives represented by the following general formula (2):

(2)

$R^1$ and $R^2$ correspond to $R^1$ and $R^2$, respectively, included in the phosphorus-containing hydroquinone derivatives represented by the aforementioned general formula (1), and $R^1$ and $R^2$ represent linear or branched alkyl groups, wherein the alkyl group has 1–18 carbon atoms, preferably 1–8 carbon atoms, and the alkyl group is more specifically exemplified by alkyl groups such as methyl, ethyl, propyl, isopropyl, tertiary butyl, cyclohexyl and so on.

Also, $R^1$ and $R^2$ may be identical or different, and $R^1$ and $R^2$ may combine together at a point other than that of a phosphorus atom to form a circular group.

Examples of $R^1$ and $R^2$ forming a circular group can be exemplified by: a propylene group; butylene group; pentamethylene group; hexamethylene group; heptamethylene group; phenylene group; biphenylene group; cyclopentylene group; cyclohexylene group; cycloheptylene group; cyclooctylene group; cyclononylene group and so on. Further, these groups may contain a hetero atom such as an oxygen atom, sulfur atom and nitrogen atom and so on within these groups. Also, X corresponds to X included in the phosphorus-containing hydroquinone derivatives represented by the aforementioned general formula (1), and X represents an oxygen atom or a sulfur atom.

Among the secondary phosphine derivatives represented by the aforementioned general formula (2), $R^1$ and $R^2$ that are capable of forming a circular group can be produced via known methods. An example thereof can be represented by the following reaction formula (1):

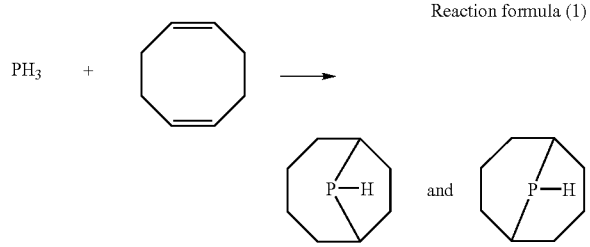

Reaction formula (1)

in which a mixture of 1,4-cyclooctylene phosphine and 1,5-cyclooctylene phosphine is obtained from 1,4-cyclooctadiene and phosphine. (Japanese Patent Application Laid-open No. S55-122790), and the resultant mixture is oxidized to obtain mixture of the target 1,4-cyclooctylene phosphine oxide and 1,5-cyclooctylene phosphine oxide.

Further, in the method of producing the phosphorus-containing hydroquinone derivatives represented by the aforementioned general formula (1), the secondary phosphine derivatives represented by the aforementioned general formula (2) form tautomer, and therefore the secondary phosphine derivatives represented by the aforementioned general formula (2) can be substituted by secondary phosphine derivatives represented by the following general formula (2a):

(2a)

(where $R^1$, $R^2$ and X are the same as represented above). Further, concerning the tautomer of the secondary phosphine derivatives represented by the aforementioned general formulas (2) and (2a), specific temperature provides one derivative of these tautomers, and the reactant material may be selected from either one of the tautomer of the secondary phosphine derivatives represented by the aforementioned general formulas (2) and (2a), or may be a mixture thereof.

The secondary phosphine derivatives represented by the aforementioned general formulas (2a) can be produced via known methods. An example can be illustrated, in which hydrochloric acid is added to diethyl phosphinous ethyl obtained via the following reaction formula (2):

$(CH_3CH_2O)_3P + 2EtMgBr \rightarrow CH_3CH_2OP(CH_2CH_3)_2 + 2CH_3CH_2OMgBr$      reaction formula (2)

to produce thereof. (KOSOLAPOFF, Vol. 4, pp. 475)

The formula of another tautomer of benzoquinone derivative is represented by the following general formula (3):

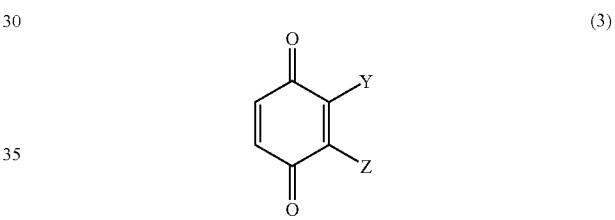

(3)

where Y and Z corresponds to Y and Z, respectively, that are included in the formula of the phosphorus-containing hydroquinone derivatives represented by the aforementioned general formula (1); and Y and Z represent: a hydrogen atom; hydroxy group; linear or branched alkyl group; aralkyl group such as benzyl and the like; allyl group, aryl group such as phenyl and the like; alkoxy group such as methoxy, ethoxy, propoxy, phenyloxy and the like; or cyano group. The alkyl group may have 1–18 carbon atoms, preferably 1–6 carbon atoms, and is more specifically exemplified by alkyl groups such as: methyl; ethyl; propyl; isopropyl; tertiary butyl; cyclohexyl and so on.

The production method of the present invention can be employed to obtain the target phosphorus-containing hydroquinone derivatives represented by the aforementioned general formula (1) by causing reaction of at least one compound selected from the secondary phosphine derivatives represented by the aforementioned general formulas (2) and (2a) with the benzoquinone derivatives represented by the aforementioned general formula (3) under the existence of an inactive solvent.

Molar ratio of the benzoquinone represented by the aforementioned general formula (3) to the secondary phosphine derivatives represented by the aforementioned general formula (2) or (2a) is generally 1.0–1.5, preferably 1.0–1.2, to 1 mole of the secondary phosphine derivatives.

Although the reaction temperature may depend on the type of the reactant materials, since temperatures in excess of 300° C. causes decomposition of the target phosphorus-containing hydroquinone derivatives represented by the aforementioned general formula (1), normally temperature of 0 to 150° C. are preferable, and 25 to 100° C. are more preferable.

The duration for the reaction may generally be 1–8 hours, and preferably 2–5 hours.

The inactive solvent is not limited to a specific solvent as long as the solvent is inactive with the aforementioned reactant materials and the target products, and can be exemplified by, for example: aromatic hydrocarbons such as benzene, toluene, xylene and the like; aliphatic hydrocarbons such as petroleum ether and the like; ethers such as dialkyl ether and the like; nitrites such as acetonitrile, propionitrile and the like; halogenated aromatic hydrocarbons such as chlorobenzene and the like; and haloalkanes such as methylene chloride, chloroform and the like, and combinations of one, two or more types of these solvents can also be used.

In addition, the production method according to the present invention can promote the reaction by acid catalysts or base catalysts as desired. Concerning the acid catalysts, one, two or more types selected from, for example: hydrochloric acid; sulfuric acid; oxalic acid; phosphoric acid; perchloric acid; periodic acid; hydrogen fluoride; methanesulfonic acid; p-tolunenesulfonic acid; benzenesulfonic acid trifluoroacetic acid; glacial acetic acid and the like can be combined for use. Concerning the base catalysts, one, two or more types selected from, for example: alkali metals such as sodium, potassium or lithium and the like; alcoxides such as sodium methoxide sodium ethoxide, potassium tert-butoxide and the like; alkyl metal compounds such as tert-butyl lithium, lithium diisopropyl amide and the like can be used. In this case, quantity of the catalyst may be generally 1–10% mol., and preferably 1–5% mol., in the compounds represented by the aforementioned general formula (3).

After completion of the reaction, filtration and drying are carried out to obtain the product, and a conventional purification may be additionally carried out as desired.

According to the aforementioned method, the phosphorus-containing hydroquinone derivative represented by the aforementioned general formula (1) can be produced, and since the derivatives include phenolic hydroxy group, direct reaction with, for example, the epoxy resin can be carried out to introduce the derivatives into the epoxy resin, or reaction with epichlorohydrin can be carried out to produce phosphorus-containing epoxy resins.

<Epoxy Resins>

Phosphorus-containing epoxy resins according to the present invention are characterized in containing a structural unit that is derived from the phosphorus-containing hydroquinone derivative represented by the aforementioned general formula (1). Here, the structural unit derived from the phosphorus-containing hydroquinone derivative represented by the aforementioned general formula (1) is meant to contain at least a structural unit represented by the following general formula (8):

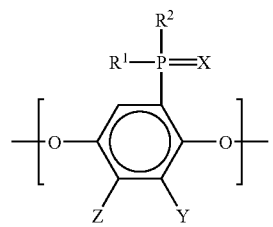

(where $R^1$, $R^2$, X, Y and Z are the same as shown above). The aforementioned phosphorus-containing hydroquinone derivatives according to the present invention are employed as one, two or more derivatives.

The method for introducing the structural unit represented by the aforementioned general formula (8) may include a method of reacting the phosphorus-containing hydroquinone derivatives represented by the aforementioned general formula (1) with epihalohydrins under the presence of a base, (hereinafter called "implementation mode 1"), or a method of reacting the phosphorus-containing hydroquinone derivatives represented by the aforementioned general formula (1) with a polyepoxy compound (hereinafter called "implementation mode 2").

<Implementation Mode 1>

Implementation mode 1 is a method of reacting the phosphorus-containing hydroquinone derivatives represented by the aforementioned general formula (1) with epihalohydrins under the presence of a base to introduce the structural unit represented by the aforementioned general formula (8) into the epoxy resin.

The aforementioned epihalohydrins are not particularly limited as long as they are available from the industry, and is preferably a compound represented by, for example, the following general formula (9):

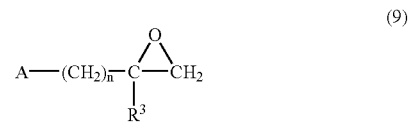

(where $R^3$ represents hydrogen atom or methyl group, A represents halogen and n is an integer from 1–5); and more specifically, the halohydrins may be preferably exemplified by: epi chlorhydrin; epi bromohydrin; epi iodichydrin; β-methyl epi chlorhydrin; β-methyl epi bromohydrin; and so on, and more preferably epi clorhydrin, because it is acquirable from the industry and the cost is low.

In such reaction, the molecular number of the resultant phosphorus-containing epoxy resins can be designed by selecting the quantity of the aforementioned epihalohydrins and the reaction conditions and the like, and the molar ratio of the aforementioned epihalohydrins may be generally 2–10 times, preferably 2–4 times the mol content of the phosphorus-containing hydroquinone derivatives.

The base may be exemplified by, for example: inorganic bases such as sodium hydroxide, sodium carbonate, sodium hydrogen carbonate, potassium hydroxide, potassium carbonate, potassium hydrogen carbonate, calcium hydroxide, calcium carbonate, barium hydroxide and so on; organic bases such as trimethyl amine, N,N'-dimethyl cyclohexylamine, N,N'-diethyl cyclohexylamine, N,N'-dimethyl benzylamine, N,N'-dimethyl piperazine, N,N'-dimethyl aniline, N,N'-diethyl aniline, N,N,N',N'-tetramethyl-1,3-propanediamine, pyridine, α-picoline, β-picoline, γ-picoline, 4-ethyl morpholine, triethylene diamine, 1,3-diaza bicyclo [5,4,0] undecene, 1,8-diaza bicyclo [5,4,0]-7-undecene, N-ethyl piperidine, quinoline, isoquinoline, N,N'-diethyl piperazine, quinaldine, 2-ethyl pyridine, 4-ethyl pyridine, 3,5-lutidine, 2,6-lutidine, 4-methyl morpholine, 2,4,6-collidine and so on; ion exchange resins having pyridyl group or dimethyl aminobenzyl group, and the like, and is not particularly limited thereto.

The quantity of the base may be a level in which the hydroxy group of the phosphorus-containing hydroquinone derivatives represented by the aforementioned general formula (1) is activated and halogenated hydrogen created as byproduct can be captured, and the level is generally 1–6 that of the stoichiometry of the byproduct halogenated hydrogen, and preferably 1–3 times.

The reaction can be implemented either with or without any solvent.

The reaction temperature may be generally 80 to 150° C., and preferably 100 to 120° C.

The duration time for the reaction may be generally 1–10 hours, and preferably 2–5 hours.

After the completion of the reaction, the phosphorus-containing epoxy resin created as desired is dissolved into a solvent such as toluene and the like, and is purified by using conventional methods such as washing with water, evaporation and the like to obtain the product.

The resultant phosphorus-containing epoxy resin has an epoxy equivalence of generally 100–1000, and preferably 190–350, and has a phosphorus content of generally 5–20% weight, and preferably 7–12% weight.

Further, novolak type epoxy resins can be produced by mixing the phosphorus-containing hydroquinone derivatives represented by the aforementioned general formula (1) with polyphenols and reacting the mixture with epihalohydrins represented by the aforementioned general formula (9). If mixing is carried out, a structural unit exemplified by the aforementioned general formula (8) can be introduced into the epoxy resins as long as it is within the aforementioned phosphorus content.

Polyphenols are not particularly limited to a specific compound as long as the epoxy resins are produced by the reaction with epihalohydrins, and one, two or more selected from: bisphenol-A; bisphenol-F; 4,4'-dihydroxy diphenyl cyclohexane; 4,4'-dihydroxy-3,3'-dimethyl diphenyl propane; 4,4'-dihydroxy benzophenone; 4,4'-dihydroxy biphenyl; 1,1'-bis (4-hydroxyphenyl)ethane; 1,1'-bis (4-hydroxy phenyl)-isobutane; 2,2'-bis(4-hydroxy tert-butyl phenyl)propane; bis (2-hydroxy naphthyl) methane; 1,5-dihydroxy naphthalene; tris (4-hydroxyphenyl) methane; 1,1'-bis(4-hydroxy phenyl) ether; resorcinol; hydroquinone; pyrocathechol; saligenin; 1,3,5-trihydroxy benzene; trihydroxy diphenyl dimethylmethane; 4,4'-hydroxy phenyl; 1,5-dihydroxy naphthalene; dihydroxy diphenyl sulfon; long chain bisphenol (cashew phenol); 2,2',5,5'-tetrakis (4-hydroxyphenyl) hexane and so on, can be employed.

The resultant phosphorus-containing epoxy resins are continuously polymerized by using a polymerization initializing agent or sequentially polymerized by using a curing agent for epoxy resins, to obtain epoxy cured resin having better flame-retardancy.

<Implementation Mode 2>

Implementation mode 2 is a method of reacting the phosphorus-containing hydroquinone derivatives represented by the aforementioned general formula (1) according to the present invention with a desired polyepoxy compound to introduce the structural unit represented by the aforementioned general formula (8) into the epoxy resin.

The epoxy resins generally include monomers, oligomers and polymers that contain at least two epoxy groups in one molecule, and more specifically include: bisphenol-A type epoxy; bisphenol-F type epoxy; bisphenol-S type epoxy; phenol novolak type epoxy; cresol novolak type epoxy; naphthalene type epoxy; N-glycidyl compounds derived from aromatic amines and heterocyclic nitrogen base such as N,N'-diglycidyl aniline, triglycidyl isocyanurate, N,N,N',N'-tetraglycidyl-bis (p-aminophenyl)-methane and so on, and are not particularly limited thereto. Combinations of several of these compounds can also be used.

The quantity of the phosphorus-containing hydroquinone derivatives represented by the aforementioned general formula (1) may preferably be 0.8–15 parts by weight as P against 100 parts by weight of the aforementioned polyepoxy compounds.

The reaction temperature may be generally -10 to 200° C., and preferably 70 to 150° C.

The reaction may be carried out under the presence of a catalyst as desired. The catalyst includes one two or more of, for example: tertiary amines such as benzyl dimethyl amine and the like; ammonium salts such as tetramethyl ammonium chloride and the like; phosphines such as triphenyl phosphine, tris(2,6-dimethoxyphenyl) phosphine and the like; phosphonium salt such as ethyl triphenyl phosphonium bromide and the like; and imidazoles such as 2-methylimidazole, 2-ethyl-4-methylimidazole and the like.

The reaction may also be carried out with employing a reaction solvent as desired, and the available reaction solvents include, for example: aromatic hydrocarbons such as benzene, toluene, xylene and the like; aliphatic hydrocarbons such as petroleum ether and the like; nitrites such as acetonitrile, propionitrile and the like; halogenated aromatic hydrocarbons such as chlorobenzene and the like; haloalkanes such as chloroform, methylene chloride and the like; N-methylpyrrolidone; dimethyl formamide; tetra hydrofuran; dioxane; dialkyl ether; glycol ether and the like, and combination of one, two or more types of these solvent can also be used.

The resultant phosphorus-containing epoxy resin has an epoxy equivalence of generally 100–1000 g/eq., and preferably 200–300 g/eq., and has a phosphorus content of generally 3–15% weight, and preferably 4–10% weight.

The resultant phosphorus-containing epoxy resins can be continuously polymerized by using a polymerization initializing agent or sequentially polymerized by using a curing agent for epoxy resins, to obtain epoxy cured resin compounds having better flame-retardancy.

<Flame-Retardant Epoxy Resin Compositions>

The flame-retardant epoxy resin compositions according to the present invention include at least one phosphorus-containing epoxy resin obtained in the aforementioned implementation mode 1 or the implementation mode 2 and a curing agent or a polymerization initializing agent.

The aforementioned polymerization initializing agents are not limited to a specific polymerization initializing agent as long as the agent helps polymerization of the phosphorus-containing epoxy resins, and one, two or more of, for example: cationic polymerization initializing agents such as methane sulfonic acid, aluminum chloride, stannum chloride, trifluoroboron ethylamine complex, trifluoroboron ethylether complex and the like; radical polymerization initializing agents such as benzoyl peroxide, azo bis-isobutyronitrile and the like; and anionic polymerization initializing agents such as methoxy potassium, triethyl amine, 2-dimethyl aminophenol and the like may be used.

The aforementioned curing agents include any agent known by a person skilled in the art, and specifically include: linear aliphatic diamines of $C_2$–$C_{20}$ such as ethylene diamine, trimethylene diamine, tetramethylene diamine, hexamethylene diamine and the like; amines such as meta phenylene diamine, para phenylene diamine, para xylene diamine, 4,4'-diamino diphenyl methane, 4,4'-diamino diphenyl propane, 4,4'-diamino diphenyl ether, 4,4'-diamino diphenyl sulfon, 4,4'-diamino dicyclohexane, bis (4-aminophenyl) phenyl methane, 1,5-diamino naphthalene, meta xylylene diamine, para xylylene diamine, 1,1-bis (4-aminophenyl) cyclohexane, dicyano amide and the like; novolak type phenolic resins such as phenol novolak resins, cresol novolak resins, tert-butyl phenol novolak resins, nonyl phenol novolak resins and the like; resol phenolic resins; poly oxystyrenes such as poly paraoxy styrene and the like; phenolic resins that are obtained by co-condensation of carbonyl compounds and phenolic compounds that are obtained by substituting hydrogen bonded to aromatic rings such as benzene ring or naphthalene ring with hydroxy group, such as naphthol type aralkyl resins; and oxide anhydrates such as pyromellitic acid anhydrate, and combinations of one, two or more types of these solvents can also be used.

The quantity of the aforementioned polymerization initializing agent may generally be 0.1–10% mol., and preferably be 0.5–2% mol against the aforementioned phosphorus-containing epoxy resins.

The quantity of the aforementioned curing agent may be added corresponding to the epoxy equivalent of the epoxy resins.

Here, the polymerization reaction may be carried out under the presence of a catalyst as desired.

The available catalyst includes: tertiary amines such as 1,8-diaza bicyclo [5,4,0] undecene-7, triethylene diamine, benzyl dimethyl amine and the like; imidazoles such as 2-methylimidazole, 2-ethyl-4-methylimidazole, 2-phenyl imidazole, 2-phenyl-4-methylimidazole and the like; organic phosphine compounds such as triphenyl phosphine, tributyl phosphine and the like; phosphonium salts; and ammonium salts and so on, and one, two or more of these can be used.

Also in this case, the polymerization reaction can be carried out by mixing this with other polyepoxy compounds. The polyepoxy compounds generally include monomers, oligomers and polymers that contain at least two epoxy groups in one molecule, and the polyepoxy compounds specifically include, for example: bisphenol-A type epoxy; bisphenol-F type epoxy; bisphenol-S type epoxy; phenol novolak type epoxy; cresol novolak type epoxy; naphthalene type epoxy; biphenyl type epoxy; N-glycidyl compounds derived from aromatic amines and heterocyclic nitrogen base such as N,N'-diglycidyl aniline, triglycidyl isocyanurate, N,N,N',N'-tetraglycidyl-bis (p-aminophenyl)-methane and so on, and are not particularly limited thereto. Combinations of several of these compounds can also be used.

The phosphorus-containing epoxy resins obtained in the aforementioned implementation mode 1 or the implementation mode 2 can also be employed in combination therewith, and are continuously polymerized by using a polymerization initializing agent or sequentially polymerized by using a curing agent for epoxy resins.

The quantity of the blended resins is not particularly limited, and the blended resins may be added to achieve the condition in which the P-containing quantity in the resins is 1–15% weight, and preferably 3–8% weight.

The flame-retardant epoxy resin compositions according to the present invention may include other flame-retardant agents, cure accelerators, inorganic fillers, silane coupling agents, mold release agents, coloring agents, stress relaxation agents and surfactants as required.

The other flame-retardant agents may include metal oxide hydrates, phosphorus flame-retardant agents, nitrogen-containing flame-retardant agents and so on.

The metal oxide hydrates are compounds having combustion inhibiting effects due to the endothermy and are represented by $M_mO_n \cdot xH_2O$ (where M is a metal, m and n are integers defined by the atomic valence of the metal, and x is the number of crystallization water contained), or a complex salt thereof, and more specifically include: aluminum hydroxide; magnesium hydroxide; basic magnesium carbonate; calcium hydroxide; barium hydroxide; zirconium hydroxide, dawsonite; zinc stannate; zinc borate; aluminum borate; stibium pentoxide; basic zinc carbonate; cobalt oxide; zirconium oxide; stannum oxide; aluminum oxide; titanium oxide; magnesium oxide; calcium silicate; pyroborate; zinc molybdate; zinc phosphate; magnesium phosphate; hydro talcite; hydro calmite; kaoline; talc; sericite; pyrophyllite; bentonite; kaolinite; calcium sulfate; zinc sulfate and so on.

The nitrogen-containing flame-retardant agents may include melamine derivatives or guanidine compounds such as: melamine; melamine cyanurate; methylol melamine; (iso) cyanuric acid; melam; melem; melon; succino guamine; melamine sulfate; aceto guanamine sulfate; melam sulfate; guanyl melamine sulfate; melamine resins; BT resins; cyanuric acid; isocyaneric acid; isocyanuric acid derivatrives; melamine isocyanurate; benzoguanamine; acetoguanamine and so on.

The phosphorus flame-retardant agents may include, for example: triethyl phosphate; tricresyl phosphate; triphenyl phosphate; cresyl phenyl phosphate; octyl diphenyl phosphate; diethylene ethyl phosphate ester; dihydroxy propylene butyl phosphate ester; ethylene phosphate di sodium ester; methyl phosphonate; dimethyl methyl phosphonate; diethyl methyl phosphonate; ethyl phosphonate; propyl phosphonate; butyl phosphonate; 2-methyl-propyl phosphonate; tert-butyl phosphonate; 2,3-dimethyl butyl phosphonate; octyl phosphonate; phenyl phosphonate; dioctyl phenyl phosphonate; dimethyl phosphinate; methyl ethyl phosphinate; methyl propyl phosphinate; diethyl phosphinate; dioctyl phosphinate; phenyl phosphinate; diethyl phenyl phosphinate; diphenyl phosphinate; bis (4-methoxy phenyl) phosphinate; red sulfur; ammonium phosphate; ammonium polyphosphate; melamine phosphate; guanyl urea phosphate; melamine polyphosphate; guanidine phosphate; ethylene diamine phosphate salt; phosphazene; melamine methyl phosphonate salt, and so on.

One, two or more of the aforementioned other flame-retardant agents can be used.

The inorganic fillers may include: fused silica powder; crystalline silica powder; alumina; silicon nitride; aluminum nitride; boron nitride; magnesia; titanium oxide; calcium carbonate; magnesium carbonate; talc; calcium silicate; glass fiber; asbesto and the like, and one, two or more of these fillers can be used.

The aforementioned curing agents may, for example, include: tertiary amines such as 1,8-diaza bicyclo [5,4,0] undecene-7, triethylene diamine, benzyl dimethyl amine and the like; imidazole compounds such as 2-methylimidazole, 2-ethyl-4-methylimidazole, 2-phenylimidazole, 2-phenyl-4-methylimidazole and the like; organic phosphine compounds such as triphenyl phosphine, tributyl phosphine and the like; phosphonium salt; and ammonium salts and so on, and one, two or more of these can be used.

The silane coupling agents may, for example, include: epoxy silanes such as γ-glycidoxy propyl trimethoxy silane and the like; amino silanes such as N-phenyl γ-amino propyl trimethoxy silane and the like, and so on.

The mold release agents may, for example, include: aliphatic acids such as stearic acid, montanic acid, palmitinic acid, oleic acid, linoleic acid and the like; salts such as calcium salts, magnesium salts, aluminum salts, zinc salts or the like of these aliphatic acid; amides of these aliphatic acid; phosphate ester; polyethylene; bisamide; calboxyl group-containing polyolefins; natural carnauba, and so on, and one, two or more of these can be used.

The coloring agents may, for example, include: carbon black; titanium oxide and the like.

The stress relaxation agents may, for example, include: silicone gel; silicone rubber; silicone oil and the like.

The surfactants may, for example, include: polyethylene glycol aliphatic acid ester; sorbitan aliphatic acid ester; aliphatic acid mono glycerid and the like.

The flame-retardant epoxy resin compositions can be employed as a safe plastic material for copper-clad laminates used for printed wiring boards and electric circuit boards, sealant used for electric parts, molding materials, casting materials, adhesives, electrically insulating paint materials and so on.

When the flame-retardant epoxy resin compositions are used for sealing resins for sealant, the composition is preferably uniformly mixed and kneaded. The method of kneading may, for example, be carried out under heated conditions by using a roller, a kneader, a mixer and the like, and then the resultant product is cooled and crushed to form tablets and so on, thereby producing the sealant resins.

Then, the sealant resins obtained as described above are used to carry out transfer molding and the like, to seal semiconductor devices or lead frames, thereby providing semiconductor devices having better flame-retardancy and moisture resistant electric reliability. Here, the method of molding is not particularly limited, except that the aforementioned sealant resins should be used, and thus common methods can be employed.

Further, the flame-retardant epoxy resin can be dissolved into a solvent to obtain resin varnish. Available solvents preferably include non-proton type solvents, and more specifically include, for example: N-methyl pyrrolidone; dimethyl formamide; ether; diethyl ether; tetra hydrofuran; dioxane; ethyl glycol ether, propylene glycol ether and butyl glycol ether of mono alcohol optionally including branched alkyl group when having 1–6 carbon atoms; ketone; acetone; methyl ethyl ketone; methyl isopropyl ketone; methyl isobutyl ketone; cyclohexane; ester; ethyl acetate; butyl acetate; ethylene glycol acetate and methoxy propyl acetate; methoxy propanol; and other halogenated hydrocarbons and alicyclic and/or aromatic hydrocarbons, and among these, solvents such as hexane, heptane, cyclohexane, toluene and dixylene and the like are preferable. The solvent may be used alone or as a mixture thereof.

Here, in the present invention, the aforementioned solvents can also be used as solvents for the aforementioned polymerization reaction, and may be used as a resin varnish as is.

The prepared varnish may be applied onto and immersed into, the work piece such as paper, glass woven cloth, glass unwoven cloth or cloth of other material than glass, and the resultant product dried in a drying furnace at 80 to 200° C. to prepare a pre-preg, and a determined number of sheets of the obtained pre-preg are layered, heated and pressed to obtain the laminates or metal-clad laminates for a printed wiring board.

EXAMPLES

The present invention will be fully described in detail by referring to the examples, but the present invention should not be construed as being limited thereto.

<Production of Phosphine Oxide>

Production Example 1

A reactor was filled with 1843 g (16.69 mol) of 1,5-cyclo octadiene (available from Tokyo Chemical Industry Co. Ltd.) and 3750 ml of toluene, and the reactor was fully purged with nitrogen. Subsequently, 731 g (21.50 mol) of phosphine (available from Nippon Chemical Industrial Co. Ltd.) was added to the reactor and the temperature was increased to 60° C. As a radical initiator, 58.8 g (0.237 mol) of 2,2-azo bis-(2,4-dimethyl valeronitrile) (available from Japan Hydrazine Company, Inc.) was introduced under pressure for 3 hours. The resultant material was aged for one night at 60° C. to obtain a toluene solution of a mixture consisting of 1,4-cyclooctylene phosphine and 1,5-cyclooctylene phosphine (purity of the mixture was 31.9% weight, the ratio of 1,4-cyclo octylene phosphine:1,5-cyclo octylene phosphine was 38.4:61.6 (GC relative areal ratio)).

A 2000 ml four-neck flask equipped with a stirrer, a condenser and a dropping funnel was fully purged with nitrogen, and thereafter a portion of the aforementioned reaction solution 434.6 g (0.975 mol) was introduced therein at room temperature. In addition, 440 g of methanol (available from Kanto Chemical Co. Ltd.) was added, and after the flask was cooled down to approximately 5° C. with an ice bath, 106.5 g (1.06 mol) of hydrogen peroxide was dropped therein via the dropping funnel for 3 hours. The end point of the reaction was determined by using the gas chromatographic method. After the completion of the oxidation reaction, the product was condensed by using a rotary evaporator to obtain 152.8 g of a mixture of colorless crystalline 1,4-cyclo octylene phosphine oxide and 1,5-cyclo octylene phosphine oxide (0.966 mol, the ratio of 1,4-cyclo octylene phosphine oxide:1,5-cyclo octylene phosphine oxide was 39.4:60.6 (NMR relative areal ratio)).

<Production of Phosphorus-Containing Hydroquinone Derivative>

Example 1

A reactor equipped with a stirrer and a temperature indicator was fed with 900 ml of toluene and 183.5 g (total purity was 87.0%, 1.00 mol) of a mixture of 1,4-cyclooctylene phosphine oxide and 1,5-cyclooctylene phosphine oxide produced in the aforementioned Production example 1 at room temperature, and the solution was stirred to be dissolved. After the reaction solution was heated to 70° C., 108.7 g (1.00 mol) of a fine powder of 1,4-benzoquinone was gradually added for 3 hours. After the completion of the adding operation, the product was aged for approximately one hour at 70° C., and thereafter the product was cooled to room temperature and filtered to obtain a precipitated product. The precipitated product was then washed with cool methanol three times and then dried under reduced pressure at 80° C. to obtain 192.7 g (0.724 mol) of a mixture of 1,4-cyclooctylene phosphonyl-1,4-hydroquinone and 1,5-cyclooctylene phosphonyl-1,4-hydroquinone in the form of buff yellow crystalline powder. The yield was 72.4%.

$^1$H NMR (300 MHz, CD$_3$OD): δ 1.43–2.83 (m, 14H), 6.67–6.91 (m, 3H);

$^{31}$P NMR (121.5 MHz, CD$_3$OD): δ 42.5 (s), 66.8 (s);

FAB-MS (Pos., m/z) 267 [M+H]$^+$;

IR (KBr, cm$^{-1}$): 3157 (υOH), 3080 (arom. υC—H), 1225 (υP=O).

Example 2

A reactor equipped with a stirrer and a temperature indicator was fed with 500 ml of toluene and 200 g (1.89 mol) of diethyl phosphine oxide at room temperature, and after the solution was heated to 70° C., 299 g (1.89 mol) of a fine powder of 1,4-naphthoquinone was gradually added for 3 hours. After the completion of the adding operation, reaction was carried out for approximately one hour at 70° C., and thereafter the product was cooled to room temperature, and filtered to obtain a precipitated product. The precipitated product was then washed with cool methanol three times and then dried under reduced pressure at 80° C. to obtain 361 g (1.37 mol) of diethyl phosphonyl-1,4-naphthalenediol in the form of a buff yellow crystalline powder. The yield was 72.3%.

$^1$H NMR (300 MHz, CD$_3$OD): δ 0.90–1.12 (m, 6H), 2.11–2.58 (m, 4H), 6.60 (s, 1H), 7.38 (m, 1H), 7.80 (m, 1H), 8.07 (m, 2H);

$^{31}$P NMR (121.5 MHz, CD$_3$OD): δ 54.0 (s), 78.5 (s);

IR (KBr, cm$^{-1}$): 3179 (υOH), 3090 (arom. υC—H), 1205 (υP=O).

Example 3

In the method of Example 2, in place of diethyl phosphine oxide, 253 g of diethyl phosphinous ethyl was dissolved into 500 ml of toluene, and the solution was reacted with 500 ml of 3 mol/L hydrochloric acid at 25° C. After the completion of the reaction, the reaction solution was separated, and a separated organic phase was washed twice with 500 ml of 5% mol aqueous sodium hydrogen carbonate and 500 ml of water. After the solution was heated to 70° C. as in Example 2, 299 g (1.89 mol) of a fine powder of 1,4-naphthoquinone was gradually added for 3 hours. After the completion of the adding operation, reaction was carried out for approximately one hour at 70° C., and thereafter the product was cooled to room temperature, and filtered to obtain a precipitated product. The precipitated product was then washed with cool methanol three times and then dried under reduced pressure at 80° C. to obtain 320 g (1.21 mol) of diethyl phosphonyl-1,4-naphthalenediol in a form of buff yellow crystalline powder. The yield was 64.0%.

Example 4

A reactor similar to that of Example 1 was fed with 750 ml of toluene and 263.6 g (total purity was 90.0%, 1.50 mol) of a mixture of 1,4-cyclooctylene phosphine oxide and 1,5-cyclooctylene phosphine oxide at room temperature, and the solution was stirred to be dissolved. After the reaction solution was heated to 100° C., a slurry-like composition of 237.4 g (1.50 mol) of 1,4-naphthoquinone and 1100 ml of toluene was gradually dropped therein for 6 hours. After the completion of the dropping operation, the product was aged for approximately two hours at 100° C., and thereafter the product was cooled to room temperature, and filtered to obtain a precipitated product. The precipitated product was then washed with cool methanol three times and then dried under reduced pressure at 80° C. to obtain 302.22 g (0.955 mol) of a mixture of 1,4-cyclooctylene phosphonyl-1,4-naphthalenediol and 1,5-cyclooctylene phosphonyl-1,4-naphthalenediol in the form of a buff yellow crystalline powder. The yield was 63.6%.

$^1$H NMR (300 MHz, CD$_3$OD): δ 1.67–2.70 (m, 14H), 6.63 (s, 1H), 7.40 (m, 1H), 7.81 (m, 1H), 8.10 (m, 2H);

$^{31}$P NMR (121.5 MHz, CD$_3$OD): B 55.3 (s), 79.8 (s);

DI—EI (m/z) 316;

IR (KBr, cm$^{-1}$): 3179 (υOH), 3090 (arom. υC—H), 1205 (υP=O).

<Production of Phosphorus-containing Epoxy Resins>

Example 5

A reactor equipped with a stirrer, a temperature indicator, a dropping funnel and a Deanstark water separator was fed with 100 g (0.376 mol) of the mixture of hydroquinone derivatives synthesized in the Example 1 and 83.4 g (0.902 mol) of epichlorohydrin, and the solution was heated and refluxed at 120° C. while the solution was stirred. Therein, 115 g (1.00 mol) of 40% by weight aqueous sodium hydroxide was dropped so as to moderately maintain the reflux. Meanwhile, water accumulated in the Deanstark water separator was appropriately discharged. After the completion of the dropping of aqueous sodium hydroxide, excessive epichlorohydrin was removed under the reduced pressure, and 500 ml of toluene was added. The toluene suspension was washed with 500 ml of water three times, and further, toluene was fractionated and removed under reduced pressure to obtain epoxy resin (A). The yield was 97%. The epoxy equivalence was 202 g/eq. P content was 8.1% by weight.

IR (KBr, cm$^{-1}$): 3080 (arom. υC-H), 1225 (υP=O), 910 (epoxy group).

Example 6

A reactor equipped with a stirrer, a temperature indicator, a dropping funnel and a Deanstark water separator was fed with 99.3 g (0.376 mol) of hydroquinone derivatives synthesized in the Example 2 and 83.4 g (0.902 mol) of epichlorohydrin, and the solution was heated and refluxed at 120° C. while the solution was stirred. Therein, 115 g (1.00 mol) of 40% weight aqueous sodium hydroxide was dropped so as to moderately maintain the reflux. Meanwhile, water accumulated in the Deanstark water separator was appropriately discharged. After the completion of the dropping of aqueous sodium hydroxide, excessive epichlorohydrin was removed under the reduced pressure, and 500 μm of toluene was added. The toluene suspension was washed with 500 ml of water three times, and further, toluene was fractionated and removed under reduced pressure to obtain epoxy resin (B). The yield was 97%. The epoxy equivalence was 214 g/eq. Phosphorus content was 7.4% by weight.

IR (KBr, cm$^{-1}$): 3080 (arom. $\upsilon$C—H), 1225 ($\upsilon$P=O), 910 (epoxy group).

Example 7

6.20 g (0.0231 mol) of phosphorus-containing hydroquinone derivative prepared in the Example 1 was added to 9.00 g of EPIKOTE 828 (available from Yuka-Shell Epoxy Co. Ltd., epoxy equivalence: 184–194) while the mixture was stirred, and was heated to 150° C. After 30 minutes, a clear fused material was formed. The mixture was further stirred at 150° C. for one hour, and then the fused material was cooled and pestled in a mortar to obtain 14.1 g of epoxy resin (C). The epoxy equivalence was 611–682 g/eq. Phosphorus content was 3.9–5.1% by weight.

Example 8

A reactor equipped with a stirrer, a temperature indicator, a dropping funnel and a Deanstark water separator was fed with 110.6 g (0.350 mol) of hydroquinone derivatives synthesized in the Example 4 and 92.52 g (1.00 mol) of epichlorohydrin, and the solution was heated and refluxed at 120° C. while the solution was stirred. Therein, 115 g (1.00 mol) of 40% by weight aqueous sodium hydroxide was dropped so as to moderately maintain the reflux. Meanwhile, water accumulated in the Deanstark water separator was appropriately discharged. After the completion of the dropping of aqueous sodium hydroxide, excessive epichlorohydrin was removed under the reduced pressure, and 500 lm of toluene was added. The toluene suspension was washed with 500 ml of water three times, and further, toluene was fractionated and removed under the reduced pressure to obtain epoxy resin (D). The yield was 96%. The epoxy equivalence was 210 g/eq. Phosphorus content was 7.2% by weight.

IR (KBr, cm$^{-1}$): 3080 (arom. $\upsilon$C—H), 1225 ($\upsilon$P=O), 910 (epoxy group).

<Production of Phosphorus-containing Epoxy Resin Compounds and Cured Compositions>

Example 9

6.2 g (45.6 mmol) of meta xylylene diamine was added to 10.0 g of epoxy resin (A) synthesized in Example 5 to form phosphorus-containing epoxy resin compound. Then, the phosphorus-containing epoxy resin compound was fully stirred at room temperature, and cured for 3 hours at room temperature and additionally for two hours at 100° C. to obtain an epoxy resin cured compound.

IR (KBr, cm$^{-1}$): 3300 ($\upsilon$N—H), 3080 (arom. $\upsilon$C—H), 1225 ($\upsilon$P=O).

Tg (DSC method): 82° C.

Example 10

9.9 g (45.4 mmol) of pyromellitic acid anhydrate was added to 10.0 g of epoxy resin (A) synthesized in Example 5 to form a phosphorus-containing epoxy resin compound. Then, the phosphorus-containing epoxy resin compound was fully stirred at room temperature, and cured for 3 hours at room temperature and additionally for two hours at 100° C. to obtain an epoxy resin cured compound.

IR (KBr, cm$^{-1}$): 3080 (arom. $\upsilon$C—H), 1720 ($\upsilon$C=O), 1225 ($\upsilon$P=O).

Tg (DSC method): 98° C.

Example 11

4.0 g (47.6 mmol) of dicyano amide was added to 10.0 g of epoxy resin (A) synthesized in Example 5 to form a phosphorus-containing epoxy resin compound. Then, the phosphorus-containing epoxy resin compound was fully stirred at room temperature, and cured for 3 hours at 100° C. and additionally for one hour at 150° C. to obtain an epoxy resin cured compound.

IR (KBr, cm$^{-1}$): 3290 ($\upsilon$N—H), 2290 ($\upsilon$CN), 3080 (arom. $\upsilon$C—H), 1225 ($\upsilon$P=O);

Tg (DSC method): 118° C.

Example 12

650 mg (4.58 mmol) of trifluoro boron ethyl ether complex was added to 10.0 g of epoxy resin (A) synthesized in Example 5 to form phosphorus-containing epoxy resin compound. Then, the phosphorus-containing epoxy resin compound was fully stirred at room temperature, and aged all day and night to obtain an epoxy resin cured compound.

IR (KBr, cm$^{-1}$): 3085 (arom. $\upsilon$C—H), 1225 ($\upsilon$P=O);

Tg (DSC method): 62° C.

Example 13

5.81 g (42.7 mmol) of meta xylylene diamine was added to 10.0 g of epoxy resin (B) synthesized in Example 6 to form a phosphorus-containing epoxy resin compound. Then, the phosphorus-containing epoxy resin compound was fully stirred at room temperature, and cured for 3 hours at room temperature and additionally for two hours at 120° C. to obtain an epoxy resin cured compound.

IR (KBr, cm$^{-1}$): 3286 ($\upsilon$N—H), 3031 (arom. $\upsilon$C—H), 1222 ($\upsilon$P=O);

Tg (DSC method): 101° C.

Example 14

9.31 g (42.7 mmol) of pyromellitic acid anhydrate was added to 10.0 g of epoxy resin (B) synthesized in Example 6 to form phosphorus-containing epoxy resin compound. Then, the phosphorus-containing epoxy resin compound was fully stirred at room temperature, and cured for 3 hours at room temperature and additionally for two hours at 120° C. to obtain an epoxy resin cured compound.

IR (KBr, cm$^{-1}$): 3032 (arom. $\upsilon$C—H), 1720 ($\upsilon$C=O), 1222 ($\upsilon$P=O);

Tg (DSC method): 106° C.

Example 15

7.07 g (51.9 mmol) of meta xylylene diamine was added to a mixture of 1.00 g of epoxy resin (B) synthesized in Example 6 with 9.00 g of EPIKOTE 828 (available from Yuka-Shell Epoxy Co. Ltd., epoxy equivalence: 184–194) to form a phosphorus-containing epoxy resin compound. Then, the phosphorus-containing epoxy resin compound was fully stirred at room temperature, and cured for 3 hours at room temperature and additionally for two hours at 120° C. to obtain an epoxy resin cured compound.

IR (KBr, cm$^{-1}$): 3300 ($\upsilon$N—H), 3075 (arom. $\upsilon$C—O), 1225 ($\upsilon$P=O);

Tg (DSC method): 101° C.

Example 16

The phosphorus-containing epoxy resin (C) obtained in Example 7 was fused at 120° C., and 2.5 g of dicyan diamide and 0.3 g of imidazole were added thereto to form a phosphorus-containing epoxy resin compound. Then the phosphorus-containing epoxy resin compound was fully mixed and cured for 4 hours at 150 to 180° C. to obtain an epoxy resin cured compound.

IR (KBr, cm$^{-1}$): 3290 ($\upsilon$N—H), 3040 (arom. $\upsilon$C—O), 2285 ($\upsilon$C≡N), 1225 ($\upsilon$P=0);

Tg (DSC method): 107° C.

Example 17

7.90 g (58.0 mmol) of meta xylylene diamine was added to 12.2 g of phosphorus-containing epoxy resin (D) obtained in Example 8 to form a phosphorus-containing epoxy resin compound. Then, the phosphorus-containing epoxy resin compound was fully stirred at room temperature, and cured for 3 hours at room temperature and additionally for two hours at 120° C. to obtain an epoxy resin cured compound.

IR (KBr, cm$^{-1}$): 3283 ($\upsilon$N—H), 3030 (arom. $\upsilon$C—H), 1223 ($\upsilon$P=0);

Tg (DSC method): 110° C.

<Flame-Retardancy Tests>

Flame-retardancy tests were carried out on the epoxy resin cured compounds prepared by Examples 9, 10, 11, 12, 13, 14, 15, 16 and 17, in which a resin plate, fabricated to have a dimension of length 125 mm×width 13 mm×thickness 3 mm, was tested according to Vertical Burning Tests designated in accordance with materials classified by UL94 (94V-0, 94V-1 and 94V-2).

The results are shown in Table-1.

TABLE-1

| Example | P content (wt %) | Glass transition Temperature (° C.) | UL-94 |
| --- | --- | --- | --- |
| 9 | 5.7 | 82 | V-0 |
| 10 | 5.0 | 98 | V-0 |
| 11 | 6.4 | 118 | V-0 |
| 12 | 7.6 | 62 | V-0 |
| 13 | 5.6 | 101 | V-0 |
| 14 | 4.9 | 106 | V-0 |
| 15 | 5.6 | 101 | V-0 |
| 16 | 5.9 | 107 | V-0 |
| 17 | 5.8 | 110 | V-0 |

<Chemical Resistance Tests>

Example 18

The epoxy resin cured compounds obtained in Example 9 and Example 17 were employed along with an epoxy resin cured compound for comparison (Comparative Example) which was obtained by adding an additive-type flame-retardant agent that is 10% weight of tricresyl phosphate into a mixture of 300 g of EPIKOTE 828 and 215 g (1.58 mol) of meta xylylene diamine and cured for two hours at 100° C. Chemical resistance tests were carried out on the three resins in accordance with JIS K-7114.

Each of the resin cured compounds are cut to a disk shaped plate of 50 mm diameter and 3 mm thickness to prepare five test specimens, respectively. These test specimens were immersed into 10 w/w % (1000 ml) sulfuric acid at 23° C. for 7 days, and thereafter fully washed, and after drying under reduced pressure all day and night at 90° C., the weight and the appearance thereof were investigated.

The results show that the respective resin cured compounds of Examples 9 and 17 exhibited a mean weight reduction of 2%, but no change in their appearance was observed. The resin cured compound prepared by adding 10% weight of tricresyl phosphate into EPIKOTE 828 exhibited a mean weight reduction of greater than 10%, and all of these specimens exhibited a hazy appearance. It was felt that such differences occur for the following reason. The epoxy resins prepared according to the present invention have P, which is bonded via P—C covalent bond, thereby providing higher chemical resistance. On the contrary, since phosphate esters such as tricresyl phosphate has P, which is bonded via P—O—C bond, hydrolysis thereof occurs to elute from the resin. It is inferred that, for this reason, the weight of the resin was significantly reduced and exhibited a hazy appearance.

<Production of Phosphorus-containing Laminates>

Example 19

Epoxy resins (A) and (D) obtained in Examples 5 and 8, respectively, were respectively added to methyl ethyl ketone, and uniformly stirred to obtain resin varnishes. The resin varnish was applied onto a glass cloth, and the resultant cloth was dried in an immersion drying furnace at 150° C. to obtain a pre-prig. Four plies of the pre-preg were layered, and heated at 160° C. under a pressure of 3.0 MPa (30 Kg/cm$^2$) to obtain laminates.

Example 20

Three sheets of the pre-preg obtained in the Example 19 and a copper sheet for printed wiring board were layered, and heated at 170° C. under a pressure of 3.0 MPa (30 Kg/cm$^2$) to obtain a cupper laminate for a printed wiring board.

<Production of Phosphorus-containing Sealant>

Example 21

A mixture of respectively, 113.98 parts of the epoxy resin (A) synthesized in Example 5 and the epoxy resin (D) synthesized in Example 8, 61.50 parts of a phenolic resin (available from Gun-ei Chemical Co. Ltd, PSM4261), 2.26 parts of triphenyl phosphine (available from Hokko Chemical CO. Ltd.), 1.13 part of OP Wax (available from Hoechst), 1.13 part of carbon black (available from Mitsubishi Chemical Co. Ltd.) and 820.0 parts of fused silica (available from Nippon Chemical Industrial Co. Ltd., SILSTAR M2430) was mixed at ambient temperature in a mixer, and kneaded by using a biaxial thermal roller at 80 to 85° C. for 7 minutes, and thereafter, was detached, cooled and crushed to prepare an epoxy resin sealant. Using the sealant, an 80-pin flat package of 19×14×2.7 mm including a test-purpose silicone chip of 6×6×0.4 mm that is provided with aluminum wiring having wire width of 10 μm and thickness of 1 μm was prepared by transfer molding.

INDUSTRIAL APPLICABILITY

As described above, the present invention can provide the phosphorus-containing hydroquinone derivatives represented by general formula (1), and provides an advantageous effect in which the derivatives are available to use as, for example, intermediate materials for a reactive flame-retardant agent or phosphorus-containing epoxy resin, since the derivatives contain a phenolic OH group.

Also, the producing method according to the present invention provides an advantageous effect of being available for producing the phosphorus-containing hydroquinone derivatives in an industrially advantageous manner.

Further, the phosphorus-containing epoxy resins derived from the phosphorus-containing hydroquinone derivatives obtained according to the present invention provide better flame-retardancy, and are available for production in an industrially advantageous manner, and in addition, since the flame-retardant epoxy resin compounds including the phosphorus-containing epoxy resins, the curing agents or the polymerizing initiator exhibit better flame-retardancy and better chemical resistance, it is useful to use the compounds for adding flame-retardancy to printed wiring boards, copper-clad laminates, sealant used for electric parts, molding materials, casting materials, adhesives, electrically insulating paint materials and so on.

The invention claimed is:

1. A phosphorus-containing hydroquinone derivative represented by a general formula (1):

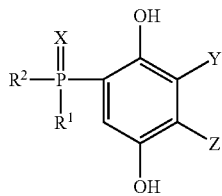

(1)

where $R^1$ and $R^2$ combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group.

2. A method for producing a phosphorus-containing hydroquinone derivative represented by a general formula (1):

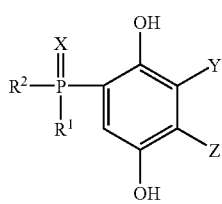

(1)

where $R^1$ and $R^2$ combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group, the method comprising:

reacting at least one compound selected from secondary phosphine derivatives represented by a general formula (2):

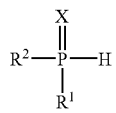

(2)

with a benzoquinone derivative represented by a general formula (3):

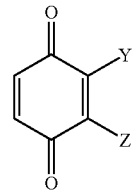

(3)

3. A method for producing a phosphorus-containing hydroquinone derivative represented by a general formula (1):

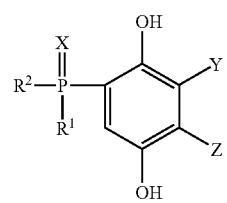

(1)

where $R^1$ and $R^2$ combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group, the method comprising:

reacting at least one compound selected from secondary phosphine derivatives represented by a general formula (2) and general formula (2a):

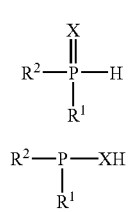

(2)

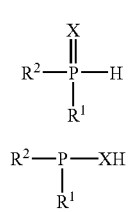

(2a)

with a benzoquinone derivative represented by a general formula (3):

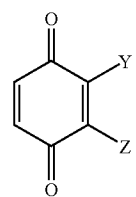

(3)

4. A phosphorus-containing epoxy resin containing a structural unit derived from a phosphorus-containing hydroquinone derivative represented by a general formula (1):

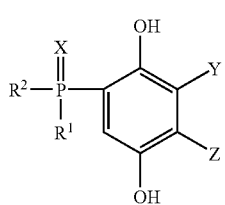

(1)

where R¹ and R² combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group.

5. The phosphorus-containing epoxy resin according to claim 4, wherein the phosphorus-containing epoxy resin is obtainable by reacting a phosphorus-containing hydroquinone derivative represented by said general formula (1) with a polyepoxy compound.

6. A flame-retardant epoxy resin composition comprising:
a phosphorus-containing epoxy resin containing a structural unit derived from a phosphorus-containing hydroquinone derivative represented by a general formula (1):

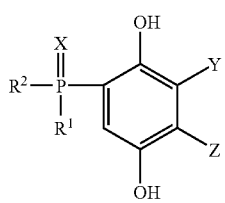

(1)

where R¹ and R² combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and
a curing agent or a polymerization initiator.

7. The flame-retardant epoxy resin composition according to claim 6, wherein the phosphorus-containing epoxy resin is obtainable by reacting a phosphorus-containing hydroquinone derivative represented by said general formula (1) with a polyepoxy compound.

8. A sealant comprising:
a flame-retardant epoxy resin composition comprising:
a phosphorus-containing epoxy resin containing a structural unit derived from a phosphorus-containing hydroquinone derivative represented by a general formula (1);

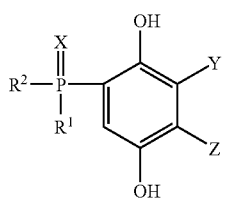

(1)

where R¹ and R² combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and
a curing agent or a polymerization initiator.

9. The sealant according to claim 8, wherein the phosphorus-containing epoxy resin is obtainable by reacting a phosphorus-containing hydroquinone derivative represented by said general formula (1) with a polyepoxy compound.

10. A laminate comprises:
a flame-retardant epoxy resin composition comprising:
a phosphorus-containing epoxy resin containing a structural unit derived from a phosphorus-containing hydroquinone derivative represented by a general formula (1);

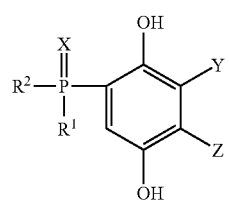

(1)

where R¹ and R² combine together to form a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and
a curing agent or a polymerization initiator.

11. The laminate according to claim 10, wherein the phosphorus-containing epoxy resin is obtainable by reacting a phosphorus-containing hydroquinone derivative represented by said general formula (1) with a polyepoxy compound.

12. A phosphorus-containing hydroquinone derivative represented by a general formula (1):

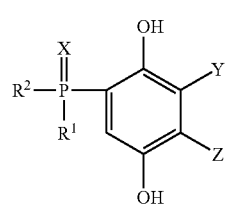

(1)

where R¹ and R² represent linear or branched alkyl groups that are identical or different, and R¹ and R² may combine together to form a circular group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and
wherein the phosphorus-containing hydroquinone derivative includes an oxygen atom or sulfur atom attached to 1,4-cyclooctylene phosphonyl1,4-hydroquinone or 1,5-cyclooctylene phosphonyl-1,4-hydroquinone or mixture thereof.

13. A method for producing a phosphorus-containing hydroquinone derivative represented by a general formula (1):

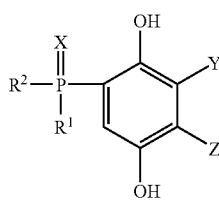

(1)

where $R^1$ and $R^2$ represent linear or branched alkyl groups that are identical or different, and $R^1$ and $R^2$ may combine together to form a circular group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group, the method comprising the steps of:

reacting at least one compound selected from secondary phosphine derivatives represented by a general formula (2):

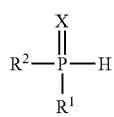

(2)

with a benzoquinone derivative represented by a general formula (3):

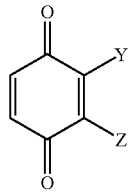

(3)

producing the phosphorus-containing hydroquinone derivative including an oxygen atom or sulfur atom attached to 1,4-cyclooctylene phosphonyl-1,4-hydroquinone or 1,5-cyclooctylene phosphonyl-1,4-hydroquinone or mixture thereof.

14. A method for producing a phosphorus-containing hydroquinone derivative represented by a general formula (1):

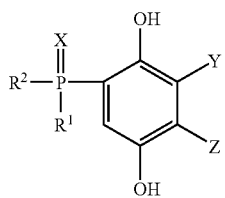

(1)

where $R^1$ and $R^2$ represent linear or branched alkyl groups that are identical or different, and $R^1$ and $R^2$ may combine together to form a circular group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group, the method comprising:

reacting at least one compound selected from secondary phosphine derivatives represented by a general formula (2) and general formula (2a):

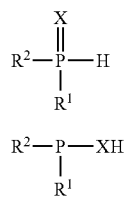

(2)

(2a)

with a benzoquinone derivative represented by a general formula (3):

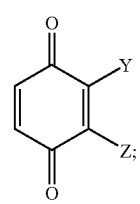

(3)

and producing the phosphorus-containing hydroquinone derivative including an oxygen atom or sulfur atom attached to 1,4-cyclooctylene phosphonyl-1,4-hydroquinone or 1,5-cyclooctylene phosphonyl1,4-hydroquinone or mixture thereof.

15. A method for producing a phosphorus-containing hydroquinone derivative represented by a general formula (A):

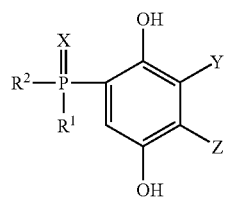

(A)

where $R^1$ and $R^2$ represent linear or branched alkyl groups that are identical or different, and $R^1$ and $R^2$ may combine together to form a circular group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group, the method comprising the steps of:

reacting at least one compound selected from secondary phosphine derivatives including 1,4-cyclooctylene phosphine oxide and 1,5-cyclooctylene phosphine oxide with a benzoquinone derivative represented by a general formula (B)

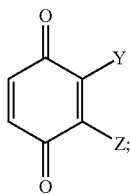
(B)

and
producing the phosphorus-containing hydroquinone derivative including an oxygen atom or sulfur atom attached to 1,4-cyclooctylene phosphonyl-1,4-hydroquinone or 1,5-cyclooctylene phosphonyl-1,4-hydroquinone or mixture thereof.

16. A phosphorus-containing hydroquinone derivative represented by a general formula (1):

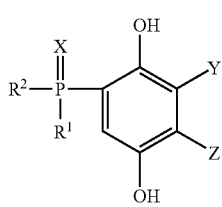
(1)

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen.

17. A method for producing a phosphorus-containing hydroquinone derivative represented by a general formula (1):

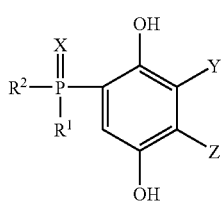
(1)

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen, the method comprising:

reacting at least one compound selected from secondary phosphine derivatives represented by a general formula (2):

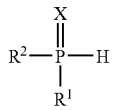
(2)

with a benzoquinone derivative represented by a general formula (3):

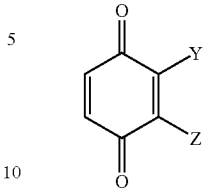
(3)

18. A method for producing a phosphorus-containing hydroquinone derivative represented by a general formula (1):

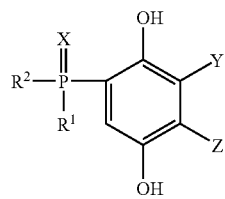
(1)

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen, the method comprising:

reacting at least one compound selected from secondary phosphine derivatives represented by a general formula (2) and general formula (2a):

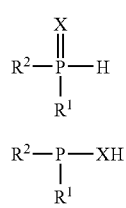
(2)

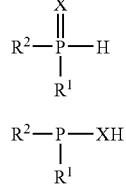
(2a)

with a benzoquinone derivative represented by a general formula (3):

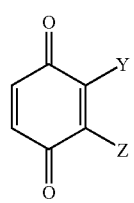
(3)

19. A phosphorus-containing epoxy resin containing a structural unit derived from a phosphorus-containing hydroquinone derivative represented by a general formula (1):

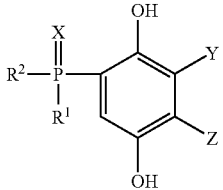

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen.

20. A flame-retardant epoxy resin composition comprising:
a phosphorus-containing epoxy resin containing a structural unit derived from a phosphorus-containing hydroquinone derivative represented by a general formula (1):

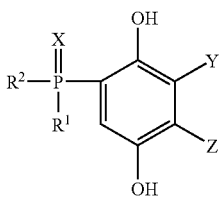

where $R^1$ and $a^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen; and
a curing agent or a polymerization initiator.

21. A sealant comprising:
a flame-retardant epoxy resin composition comprising:
a phosphorus-containing epoxy resin containing a structural unit derived from a phosphorus-containing hydroquinone derivative represented by a general formula (1);

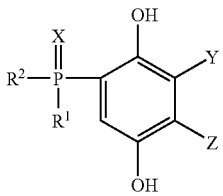

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen; and
a curing agent or a polymerization initiator.

22. A laminate comprises:
a flame-retardant epoxy resin composition comprising:
a phosphorus-containing epoxy resin containing a structural unit derived from a phosphorus-containing hydroquinone derivative represented by a general formula (1);

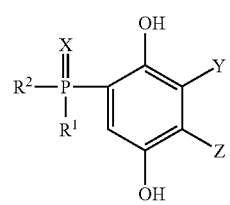

where $R^1$ and $R^2$ represent linear or branched alkyl groups that are identical or different; X represents an oxygen atom; Y and Z represent a hydrogen atom, hydroxy group, linear or branched alkyl group, aralkyl group, alkoxy group, allyl group, aryl group or cyano group, and/or Y and Z may form a circular group, wherein Y and Z cannot both be hydrogen; and
a curing agent or a polymerization initiator.

23. A phosphorus-containing epoxy resin containing a structural unit derived from a phosphorus-containing hydroguinone derivative represented by a general formula (1):

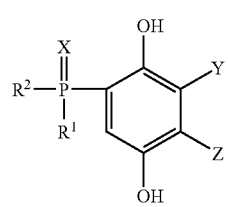

where $R^1$ and $R^2$ represent linear or branched alkyl groups that are identical or different, and $R^1$ and $R^2$ may combine together to form a circular alkyl group or a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group;
wherein the phosphorus-containing epoxy resin is obtainable by reacting a phosphorus-containing hydroquinone derivative represented by said general formula (1) with epihalohydrins.

24. A flame-retardant epoxy resin composition comprising:
a phosphorus-containing epoxy resin containing a structural unit derived from a phosphorus-containing hydroguinone derivative represented by a general formula (1):

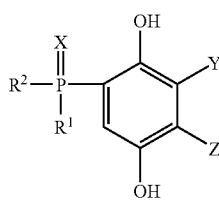

where $R^1$ and $R^2$ represent linear or branched alkyl groups that are identical or different, and $R^1$ and $R^2$ may combine together to form a circular alkyl group or a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and a curing agent or a polymerization initiator;

wherein the phosphorus-containing, epoxy resin is obtainable by reacting a phosphorus-containing hydroquinone derivative represented by said general formula (1) with epihalohydrins.

25. A sealant comprising:

a flame-retardant epoxy resin composition comprising:

a phosphorus-containing epoxy resin containing a structural unit derived from a phosphorus-containing hydroguinone derivative represented by a general formula (1);

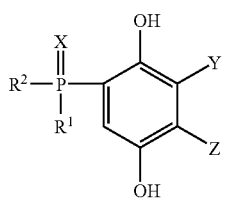

where $R^1$ and $R^2$ represent linear or branched alkyl groups that are identical or different, and R and R may combine together to form a circular alkyl group or a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and a curing agent or a polymerization initiator;

wherein the phosphorus-containing epoxy resin is obtainable by reacting a phosphorus-containing hydroquinone derivative represented by said general formula (1) with epihalohydrins.

26. A laminate comprises:

a flame-retardant epoxy resin composition comprising:

a phosphorus-containing epoxy resin containing a structural unit derived from a phosphorus-containing hydroguinone derivative represented by a general formula (1);

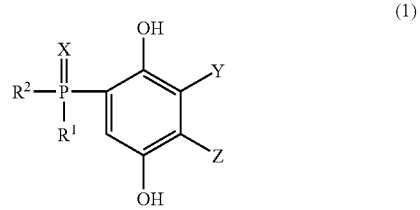

where $R^1$ and $R^2$ represent linear or branched alkyl groups that are identical or different, and $R^1$ and $R^2$ may combine together to form a circular alkyl group or a circular alkylene group; X represents an oxygen atom or sulfur atom; Y and Z represent a hydrogen atom, hydroxy group, linear or branched alkyl group, aralkyl group, alkoxy group, allyl group, aryl group or cyano group, and/or Y and Z may form a circular group; and a curing agent or a polymerization initiator;

wherein the phosphorus-containing epoxy resin is obtainable by reacting a phosphorus-containing hydroquinone derivative represented by said general formula (1) with epihalohydrins.

* * * * *